United States Patent
Noergaard

(10) Patent No.: US 12,024,542 B2
(45) Date of Patent: Jul. 2, 2024

(54) MATING FACTOR ALPHA PRO-PEPTIDE VARIANTS

(71) Applicant: Novo Nordisk A/S, Bagsvaerd (DK)

(72) Inventor: Per Noergaard, Humlebaek (DK)

(73) Assignee: Novo Nordisk A/S, Bagsvaerd (DK)

( * ) Notice: Subject to any disclaimer, the term of this patent is extended or adjusted under 35 U.S.C. 154(b) by 131 days.

(21) Appl. No.: 17/687,755

(22) Filed: Mar. 7, 2022

(65) Prior Publication Data

US 2022/0194995 A1 Jun. 23, 2022

Related U.S. Application Data

(63) Continuation of application No. 16/573,586, filed on Sep. 17, 2019, which is a continuation of application No. 15/121,050, filed as application No. PCT/EP2015/054298 on Mar. 2, 2015, now abandoned.

(30) Foreign Application Priority Data

Feb. 28, 2014 (EP) .................................... 14157172

(51) Int. Cl.
C07K 14/395 (2006.01)
C07K 14/605 (2006.01)
C12P 21/02 (2006.01)

(52) U.S. Cl.
CPC .......... *C07K 14/395* (2013.01); *C07K 14/605* (2013.01); *C12P 21/02* (2013.01); *C07K 2319/00* (2013.01)

(58) Field of Classification Search
CPC ............... C07K 14/395; C07K 14/605; C07K 2319/00; C12P 21/02
See application file for complete search history.

(56) References Cited

U.S. PATENT DOCUMENTS

2017/0096472 A1  4/2017 Rosen et al.

FOREIGN PATENT DOCUMENTS

| CN | 101287750 | 10/2008 |
|---|---|---|
| CN | 103333913 A | 10/2013 |
| EP | 0121884 A2 | 10/1984 |
| EP | 324274 A1 | 7/1989 |
| WO | 9211378 A1 | 7/1992 |
| WO | 95/34666 A1 | 12/1995 |
| WO | 95/35384 A1 | 12/1995 |
| WO | 9801535 A1 | 1/1998 |
| WO | 03/060071 A2 | 7/2003 |
| WO | 03062431 A2 | 7/2003 |

(Continued)

OTHER PUBLICATIONS

Naerulff S. et al., Comparison of different signal peptides for secretion of heterologous proteins in fission yeast, Biochemical and Biophysical Research Communications, Sep. 2005, vol. 336, pp. 974-982.

(Continued)

*Primary Examiner* — Randall L Beane
(74) *Attorney, Agent, or Firm* — Roemarie R. Wilk-Orescan

(57) ABSTRACT

The present invention is related to Mating Factor α pro-peptide variants useful for the recombinant expression of polypeptides comprising a GLP-1 peptide in yeasts. The invention is also related to DNA sequences, vectors and host cells for use in expressing polypeptides in yeasts.

16 Claims, 2 Drawing Sheets
Specification includes a Sequence Listing.

(56) References Cited

FOREIGN PATENT DOCUMENTS

| WO | 2005100388 A1 | 10/2005 |
| WO | 2008032659 A1 | 3/2008 |

OTHER PUBLICATIONS

Lin-Cereghino G. P. et al., The effect of á-mating factor secretion signal mutations on recombinant protein expression in Pichia pastoris, Gene, Feb. 2013, vol. 519, No. 2, pp. 311-317, EP A SR, WO A SR.
Otte S. et al., Sorting signals can direct receptor-mediated export of soluble proteins into COPII vesicles, Nature Cell Biology, Oct. 2004, vol. 6, No. 12, pp. 1189-1194.
Rakestraw J. A. et al.,Directed Evolution of a Secretory Leader for the Improved Expression of Heterologous Proteins and Full-Length Antibodies in *Saccharomyces cerevisiae,* Biotechnology and Bioengineering, Apr. 2009, vol. 103, No. 6, pp. 1192-1201.
Thim L. et al., Secretion and processing of insulin precursors in yeast, Proceedings of the National Academy of Sciences, Sep. 1986, vol. 83, No. 18, pp. 6766-6770.
Eilert et al., "Improved Processing of Secretory Proteins in Hansenula Polymorpha by Sequence Variation Near the Processing Site of the Alpha Mating Factor Prepro Sequence," Journal of Biotechnology, 2013, vol. 167, No. 2, pp. 94-100.
Pfam05436: MF_alpha_N, 1 page, also available at https://www.ncbi.nlm.nih.gov/Structure/cdd/cddsrv.cgi?uid=pfam05436 (last visited May 29, 2018) (Year: 2018).
GI 74605649, Q6CMM2, Similar to sp|Q8J094 Saccharoxus paradoxus Alpha-pheromone, NCBI (submitted 2004), also available at https://www.ncbi.nlm.nih.gov/protein/74605649 (last visited Aug. 20, 2018) (Year: 2004).
Gordon et al., "Evolutionary erosion of yeast sex chromosomes by mating-type switching accidents," PNAS, Dec. 13, 2011, vol. 180, No. 50, pp. 20024-20029.
XP_003644796, Hypothetical protein Ecym_2232 [Eremothecium cymbalariae DBVPG#7215], NCBI (submitted 2011), also available at https://www.ncbi.nlm.nih.gov/protein/363749157 (last visited Aug. 20, 2018) (Year: 2011).
XP_003956110 (i.e., gi410077056), Hypothetical protein KAFR_0B06780 [Kazachstania Africana CBS 2517], NCBI (submitted 2011), also available at https://www.ncbi.nlm.nih.gov/protein/410077056 (last visited Aug. 20, 2018) (Year: 2011).
XP_003956341 (i.e., gi410077519), Hypothetical protein KAFR_0C02130 [Kazachstania Africana CBS 2517], NCBI (submitted 2011), also available at https://www.ncbi.nlm.nih.gov/protein/410077519 (last visited Aug. 20, 2018) (Year: 2011).
XP_004178870 (i.e., gi444316426), Hypothetical protein TLBA_0B05180 [Tetrapisispora blattae CBS 6284], NCBI (submitted 2011), also available at https://www.ncbi.nlm.nih.gov/protein/444316426 (last visited Aug. 20, 2018) (Year: 2011).
XP_446929, Uncharacterized protein CAGLOH03135g [[Candida] giabrata], NCBI (submitted 2004), also available at https://www.ncbi.nlm.nih.gov/protein/50288999 (last visited Aug. 20, 2018) (Year: 2004).
AAC33392.1, vrID [Dichelobacter nodosus], GenBank: AAC33392.1, NCBI (submitted 1995), also available at https://www.ncbi.nlm.nih.gov/protein/AAC33392 (last visited Aug. 20, 2018) (Year: 1995).
Genbank AGW24974.1, mating factor alpha 1 [*Saccharomyces paradoxus*], Sep. 25, 2013, https://www.ncbi.nlm.nih.gov/protein/AGW24974.1.
Livingstone et al., Protein sequence alignments: a strategy for the hierarchical analysis of residue conservation, CABIOS, 1993, vol. 9, No. 6, pp. 745-756.

SEQUENCE LISTING

<160> NUMBER OF SEQ ID NOS: 49

<210> SEQ ID NO 1
<211> LENGTH: 5

```
<212> TYPE: PRT
<213> ORGANISM: Artificial Sequence
<220> FEATURE:
<223> OTHER INFORMATION: MFalpha propeptide variant subsequence
<220> FEATURE:
<221> NAME/KEY: MISC_FEATURE
<222> LOCATION: (1)..(1)
<223> OTHER INFORMATION: Amino acid residue which is F, L, I or V.
<220> FEATURE:
<221> NAME/KEY: MISC_FEATURE
<222> LOCATION: (2)..(2)
<223> OTHER INFORMATION: Amino acid residue which is  L, I, V or M.
<220> FEATURE:
<221> NAME/KEY: MISC_FEATURE
<222> LOCATION: (3)..(3)
<223> OTHER INFORMATION: Amino acid residue which is  A, G, S, E, Q, Y,
      F, W, R, K, H, L, I, V or M.
<220> FEATURE:
<221> NAME/KEY: MISC_FEATURE
<222> LOCATION: (4)..(4)
<223> OTHER INFORMATION: Amino acid residue which is  S, Y, F, W, L, I,
      V or M.
<220> FEATURE:
<221> NAME/KEY: MISC_FEATURE
<222> LOCATION: (5)..(5)
<223> OTHER INFORMATION: Amino acid residue which is  Y, W, L, I, V, M
      or S.

<400> SEQUENCE: 1

Xaa Xaa Xaa Xaa Xaa
1               5

<210> SEQ ID NO 2
<211> LENGTH: 85
<212> TYPE: PRT
<213> ORGANISM: Saccharomyces cerevisiae

<400> SEQUENCE: 2

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg
                85

<210> SEQ ID NO 3
<211> LENGTH: 5
<212> TYPE: PRT
<213> ORGANISM: Artificial Sequence
<220> FEATURE:
<223> OTHER INFORMATION: Synthetic

<400> SEQUENCE: 3

Val Ile Gly Tyr Leu
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic
```

<400> SEQUENCE: 4

Val Ile Gly Tyr Ser
1               5

<210> SEQ ID NO 5
<211> LENGTH: 31
<212> TYPE: PRT
<213> ORGANISM: Homo sapiens

<400> SEQUENCE: 5

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 6
<211> LENGTH: 31
<212> TYPE: PRT
<213> ORGANISM: Artificial sequence
<220> FEATURE:
<223> OTHER INFORMATION: Analogue of GLP-1(7-37)

<400> SEQUENCE: 6

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 7
<211> LENGTH: 29
<212> TYPE: PRT
<213> ORGANISM: Artificial sequence
<220> FEATURE:
<223> OTHER INFORMATION: Analogue of GLP-1(9-37)

<400> SEQUENCE: 7

Glu Gly Thr Phe Thr Ser Asp Val Ser Ser Tyr Leu Glu Gly Gln Ala
1               5                   10                  15

Ala Lys Glu Phe Ile Ala Trp Leu Val Arg Gly Arg Gly
            20                  25

<210> SEQ ID NO 8
<211> LENGTH: 66
<212> TYPE: PRT
<213> ORGANISM: Artificial sequence
<220> FEATURE:
<223> OTHER INFORMATION: MFalpha propeptide variant L42S-MFa(20-85)

<400> SEQUENCE: 8

Ala Pro Val Asn Thr Thr Thr Glu Asp Glu Thr Ala Gln Ile Pro Ala
1               5                   10                  15

Glu Ala Val Ile Gly Tyr Ser Asp Leu Glu Gly Asp Phe Asp Val Ala
            20                  25                  30

Val Leu Pro Phe Ser Asn Ser Thr Asn Asn Gly Leu Leu Phe Ile Asn
        35                  40                  45

Thr Thr Ile Ala Ser Ile Ala Ala Lys Glu Glu Gly Val Ser Leu Asp
    50                  55                  60

Lys Arg
65

<210> SEQ ID NO 9

```
<211> LENGTH: 5
<212> TYPE: PRT
<213> ORGANISM: Artificial Sequence
<220> FEATURE:
<223> OTHER INFORMATION: Synthetic

<400> SEQUENCE: 9

Glu Glu Ala Glu Lys
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic

<400> SEQUENCE: 10

Glu Glu Ala His Lys
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic

<400> SEQUENCE: 11

Glu Glu Ala Glu Ala His Lys
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic

<400> SEQUENCE: 12

Glu Glu Ala Glu Ala Glu Ala His Lys
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic

<400> SEQUENCE: 13

Glu Glu Gly His Lys
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic

<400> SEQUENCE: 14

Glu Glu Gly Glu Pro Lys
1               5

<210> SEQ ID NO 15
<211> LENGTH: 7
```

```
<212> TYPE: PRT
<213> ORGANISM: Artificial Sequence
<220> FEATURE:
<223> OTHER INFORMATION: Synthetic

<400> SEQUENCE: 15

Glu Glu Ala His Glu Leu Lys
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic

<400> SEQUENCE: 16

Glu Glu Ala His Glu Val Lys
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic

<400> SEQUENCE: 17

Glu Glu Ala His Glu Met Lys
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic

<400> SEQUENCE: 18

Glu Glu Ala His Glu Phe Lys
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic

<400> SEQUENCE: 19

Glu Glu Ala His Glu Tyr Lys
1               5

<210> SEQ ID NO 20
<211> LENGTH: 15
<212> TYPE: PRT
<213> ORGANISM: Artificial Sequence
<220> FEATURE:
<223> OTHER INFORMATION: Synthetic

<400> SEQUENCE: 20

Glu Glu Ala His Glu Trp Lys Glu Glu Gly Asn Thr Thr Pro Lys
1               5                   10                  15

<210> SEQ ID NO 21
<211> LENGTH: 11
<212> TYPE: PRT
```

```
<213> ORGANISM: Artificial Sequence
<220> FEATURE:
<223> OTHER INFORMATION: Synthetic

<400> SEQUENCE: 21

Glu Glu Leu Asp Ala Arg Leu Glu Ala Leu Lys
1               5                   10

<210> SEQ ID NO 22
<211> LENGTH: 6
<212> TYPE: PRT
<213> ORGANISM: Artificial Sequence
<220> FEATURE:
<223> OTHER INFORMATION: Synthetic

<400> SEQUENCE: 22

Gln Pro Met Tyr Lys Arg
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic

<400> SEQUENCE: 23

Gly Gln Pro Met Tyr Lys
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic

<400> SEQUENCE: 24

Pro Gly Gln Pro Met Tyr
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic

<400> SEQUENCE: 25

Lys Pro Gly Gln Pro Met
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic

<400> SEQUENCE: 26

Leu Lys Pro Gly Gln Pro
1               5

<210> SEQ ID NO 27
<211> LENGTH: 6
<212> TYPE: PRT
<213> ORGANISM: Artificial Sequence
```

```
<220> FEATURE:
<223> OTHER INFORMATION: Synthetic

<400> SEQUENCE: 27

Gln Leu Lys Pro Gly Gln
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

Leu Gln Leu Lys Pro Gly
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic

<400> SEQUENCE: 29

Trp Leu Gln Leu Lys Pro
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic

<400> SEQUENCE: 30

His Trp Leu Gln Leu Lys
1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic

<400> SEQUENCE: 31

Trp His Trp Leu Gln Leu
1               5

<210> SEQ ID NO 32
<211> LENGTH: 6
<212> TYPE: PRT
<213> ORGANISM: Artificial Sequence
<220> FEATURE:
<223> OTHER INFORMATION: Synthetic

<400> SEQUENCE: 32

Ala Trp His Trp Leu Gln
1               5

<210> SEQ ID NO 33
<211> LENGTH: 6
<212> TYPE: PRT
<213> ORGANISM: Artificial Sequence
<220> FEATURE:
```

<223> OTHER INFORMATION: Synthetic

<400> SEQUENCE: 33

Glu Ala Trp His Trp Leu
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic

<400> SEQUENCE: 34

Ala Glu Ala Trp His Trp
1               5

<210> SEQ ID NO 35
<211> LENGTH: 6
<212> TYPE: PRT
<213> ORGANISM: Artificial Sequence
<220> FEATURE:
<223> OTHER INFORMATION: Synthetic

<400> SEQUENCE: 35

Glu Ala Glu Ala Trp His
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic

<400> SEQUENCE: 36

Asp Val Lys Pro Gly Gln Pro Leu Ala
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic

<400> SEQUENCE: 37

Asp Val Lys Pro Gly Gln Pro Glu Tyr
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic

<400> SEQUENCE: 38

Asp Val Lys Pro Gly Glu Pro Leu Tyr
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic

```
<400> SEQUENCE: 39

Asp Val Lys Pro Gly Gln Pro Leu Tyr
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic

<400> SEQUENCE: 40

Asp Val Lys Pro Gly Gln Pro Leu Glu
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic

<400> SEQUENCE: 41

Asp Val Lys Pro Gly Gln Pro Met Tyr
1               5

<210> SEQ ID NO 42
<211> LENGTH: 14
<212> TYPE: PRT
<213> ORGANISM: Artificial Sequence
<220> FEATURE:
<223> OTHER INFORMATION: Synthetic

<400> SEQUENCE: 42

Asp Val Lys Pro Gly Gln Pro Met Tyr Asp Asp Asp Lys
1               5                   10

<210> SEQ ID NO 43
<211> LENGTH: 29
<212> TYPE: PRT
<213> ORGANISM: Artificial sequence
<220> FEATURE:
<223> OTHER INFORMATION: Analogue of GLP-1(9-37)

<400> SEQUENCE: 43

Glu Gly Thr Phe Thr Ser Asp Val Ser Ser Tyr Leu Glu Gly Gln Ala
1               5                   10                  15

Ala Lys Glu Phe Ile Ala Trp Leu Val Arg Gly Arg Lys
            20                  25

<210> SEQ ID NO 44
<211> LENGTH: 45
<212> TYPE: PRT
<213> ORGANISM: Artificial sequence
<220> FEATURE:
<223> OTHER INFORMATION: Extended analogue of GLP-1(7-37)

<400> SEQUENCE: 44

Asp Val Lys Pro Gly Gln Pro Met Tyr Asp Asp Asp Lys His Ala
1               5                   10                  15

Glu Gly Thr Phe Thr Ser Asp Val Ser Ser Tyr Leu Glu Gly Gln Ala
                20                  25                  30

Ala Lys Glu Phe Ile Ala Trp Leu Val Arg Gly Arg Gly
            35                  40                  45
```

<210> SEQ ID NO 45
<211> LENGTH: 5
<212> TYPE: PRT
<213> ORGANISM: Artificial Sequence
<220> FEATURE:
<223> OTHER INFORMATION: Synthetic

<400> SEQUENCE: 45

Val Ile Asp Tyr Ser
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic

<400> SEQUENCE: 46

Val Ala Thr Tyr Leu
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic

<400> SEQUENCE: 47

Val Ile Gly Tyr Arg
1               5

<210> SEQ ID NO 48
<211> LENGTH: 5
<212> TYPE: PRT
<213> ORGANISM: Artificial Sequence
<220> FEATURE:
<223> OTHER INFORMATION: Synthetic

<400> SEQUENCE: 48

Ala Ile Gly Tyr Leu
1               5

<210> SEQ ID NO 49
<211> LENGTH: 128
<212> TYPE: PRT
<213> ORGANISM: Artificial Sequence
<220> FEATURE:
<223> OTHER INFORMATION: Synthetic

<400> SEQUENCE: 49

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Arg Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Asp Val Lys Pro Gly Gln Pro Met Tyr Asp Asp

|  | 85 |  |  |  | 90 |  |  |  | 95 |  |  |
|---|---|---|---|---|---|---|---|---|---|---|---|
| Asp | Asp | Lys | Glu | Gly | Thr | Phe | Thr | Ser | Asp | Val | Ser | Tyr | Leu | Glu |
|  |  |  | 100 |  |  |  | 105 |  |  |  | 110 |

| Gly | Gln | Ala | Ala | Lys | Glu | Phe | Ile | Ala | Trp | Leu | Val | Arg | Gly | Arg | Gly |
|  |  |  | 115 |  |  |  | 120 |  |  |  | 125 |

MATING FACTOR ALPHA PRO-PEPTIDE VARIANTS

CROSS-REFERENCE TO RELATED APPLICATIONS

This application is a continuation of U.S. application Ser. No. 16/573,586, filed Sep. 17, 2019, which is a U.S. application Ser. No. 15/121,050, filed Aug. 24, 2016 (now abandoned), which is a 35 U.S.C. § 371 national stage application of International Patent Application PCT/EP2015/054298 (published as WO 2015/128507), filed Mar. 2, 2015, which claimed priority of European Patent Application 14157172.9, filed Feb. 28, 2014; the contents of all above-named applications are incorporated herein by reference.

SEQUENCE LISTING

The instant application contains a Sequence Listing which has been submitted in ASCII format via EFS-Web and is hereby incorporated by reference in its entirety. Said ASCII copy, created on Jan. 18, 2022, is named 130089US04_SeqList.txt and is 11 kilobytes in size.

TECHNICAL FIELD

The present invention relates to the technical fields of protein expression and protein chemistry where a polypeptide is prepared by recombinant expression in yeast.

BACKGROUND

The techniques of recombinant polypeptide expression allow for the production of large quantities of desirable polypeptides which may be used for e.g. their biological activity. Such polypeptides are often expressed as recombinant fusion polypeptides in microbial host cells. The polypeptide of interest is often attached to a fusion partner polypeptide in order to increase the expression level, facilitate secretion, increase the solubility, promote polypeptide folding, to protect the polypeptide against unintentional proteolysis or to facilitate purification of the polypeptide of interest.

To ensure secretion of recombinantly expressed polypeptides from yeast, a pre-pro peptide (often called "leader") is normally fused to the N-terminus of the recombinant product. The pre-sequence ensures translocation of the fusion protein into the endoplasmic reticulum (ER), which is the starting point of the secretory pathway. The pro-sequence ensures further transport from the ER to the Golgi apparatus, where an endogenous protease called Kex2p, often are used to cleave off the pro-sequence. The processed recombinant peptide is subsequently secreted to the growth media, from where it can be purified.

The pre-pro sequence from Mating Factor Alpha is often used as leader when secreting recombinant polypeptides. However, many other sequences are able to facilitate the secretory process. The leader sequence has a significant influence, not only on the amounts of secreted peptide, but also on the quality in terms of degradation and post-translational modifications such as O-glycosylation. As degradation and O-glycosylation normally are unwanted events, it is desirable with a leader sequence that reduces these modifications to the lowest possible extent, and at the same time maximizes the yield of secreted polypeptide.

EP 0121884 A2 describes the recombinant production of human insulin in *S. cerevisiae* using yeast alpha-factor.

EP 0324274A1 describes the use of a truncated alpha-factor leader sequence for improved expression and secretion of heterologous proteins in yeast.

Thim et al. (PNAS 83 (1986) 6766-6770) describe the use of Mating Factor Alpha for secretion and processing of insulin precursors in *Saccharomyces cerevisiae*.

WO95/34666 describes synthetic leaders for producing secreted polypeptides in *S. cerevisiae*.

Rakestraw et al. (Biotech. Bioeng. 103 (2009) 1192-1201) describe mutant Mating Factor Alpha leader sequences which increase the secretion of single-chain antibody and which increase human IgG1 production levels in *S. cerevisiae*.

There is a need for more specific leader sequences which increase the yield of the polypeptide precursor, and which reduce the proportion of the recombinant polypeptide which is O-glycosylated. In particular there is a need for leader sequences for expressing GLP-1 peptides in yeast, which leaders increase the yield of the GLP-1 peptides or precursors thereof and lower the O-glycosylation of the GLP-1 peptides. Such more specific leader sequences may facilitate a higher yield of the recombinant polypeptide as well as a lower the amount of O-glycosylated impurities.

SUMMARY

It is an object of the present invention to provide yeast cells having increased level of expression of heterologous polypeptides. It is also an object of the present invention to provide yeast cells secreting recombinant polypeptide having a reduced amount of O-glycosylated variants of the recombinant polypeptide. In particular it is an object of the present invention to provide yeast cells having both an increased level of expression of the recombinant polypeptide and a reduced amount of O-glycosylated variants. It is an object of the present invention to provide improved expression system for recombinant expression of GLP-1 peptides in yeast cells.

According to a first aspect of the invention there is provided a method for recombinant expression of a polypeptide comprising a GLP-1 peptide in yeast comprising the culturing of a yeast strain comprising a DNA sequence encoding a processing and secretion signal upstream of the polypeptide, wherein said processing and secretion signal comprises a Mating Factor α pro-peptide variant having at least one substitution in the VIGYL (SEQ ID NO:3) sequence at positions 38-42 to comprise the amino acid sequence of the general formula (I):

$$X_{38}\text{-}X_{39}\text{-}X_{40}\text{-}X_{41}\text{-}X_{42} \quad \text{(I)} \quad \text{(SEQ ID NO: 1)}$$

wherein
$X_{38}$ is F, L, I or V;
$X_{39}$ L, I, V or M;
$X_{40}$ is A, G, S, E, Q, Y, F, W, R, K, H, L, I, V or M;
$X_{41}$ is S, Y, F, W, L, I, V or M;
$X_{42}$ is Y, W, L, I, V, M or S;
with the proviso that $X_{38}$-$X_{42}$ is not VIGYS (SEQ ID NO:4).

In one embodiment of the method for recombinant expression of a polypeptide in yeast the Mating Factor α pro-peptide variant has at least one substitution in the VIGYL (SEQ ID NO:3) sequence at positions 38-42 to comprise the amino acid sequence of the general formula (I):

$$X_{38}-X_{39}-X_{40}-X_{41}-X_{42} \quad (I)$$

wherein $X_{38}$ is V; $X_{39}$ L, I, V or M; $X_{40}$ is G or R; $X_{41}$ is Y, and $X_{42}$ is L.

In another embodiment the polypeptide for recombinant expression is a GLP-1 peptide.

In another embodiment the polypeptide for recombinant expression comprises GLP-1(7-37)[K34R], GLP-1(9-37)[K34R] or GLP-1(9-37)[K34R,G37K].

According to a second aspect of the invention there is provided a Mating Factor α pro-peptide variant having at least one substitution in the VIGYL (SEQ ID NO:3) sequence at positions 38-42 to comprise the amino acid sequence of the general formula (I):

$$X_{38}-X_{39}-X_{40}-X_{41}-X_{42} \quad (I)$$

wherein
- $X_{38}$ is F, L, I or V;
- $X_{39}$ L, I, V or M;
- $X_{40}$ is A, G, S, E, Q, Y, F, W, R, K, H, L, I, V or M;
- $X_{41}$ is S, Y, F, W, L, I, V or M;
- $X_{42}$ is Y, W, L, I, V, M or S;

with the proviso that $X_{38}$-$X_{42}$ is not VIGYS (SEQ ID NO:4).

According to a third aspect of the invention there is provided a GLP-1 precursor which is a fusion polypeptide comprising:

A pre-peptide,

A Mating Factor α pro-peptide variant having at least one substitution in the VIGYL (SEQ ID NO:3) sequence at positions 38-42 to comprise the amino acid sequence of the general formula (I):

$$X_{38}-X_{39}-X_{40}-X_{41}-X_{42} \quad (I) \quad (\text{SEQ ID NO: 1})$$

wherein
- $X_{38}$ is F, L, I or V;
- $X_{39}$ L, I, V or M;
- $X_{40}$ is A, G, S, E, Q, Y, F, W, R, K, H, L, I, V or M;
- $X_{41}$ is S, Y, F, W, L, I, V or M;
- $X_{42}$ is Y, W, L, I, V, M or S;
- with the proviso that $X_{38}$-$X_{42}$ is not VIGYS (SEQ ID NO:4), Optionally an extension peptide, and A GLP-1 polypeptide.

According to a fourth aspect of the invention there is provided a DNA sequence encoding the Mating Factor α pro-peptide variant or the GLP-1 precursor.

According to a fifth aspect of the invention there is provided an expression vector comprising the DNA sequence encoding the Mating Factor α pro-peptide variant or the GLP-1 precursor.

According to a sixth aspect of the invention there is provided a host cell comprising the expression vector according to the invention.

In one embodiment the host cell used for expression has a non-functional pmt1 gene or no pmt1 gene at all. Such a host cell has surprisingly been found to lower the amount of O-glycosylated polypeptide independently of, and in addition to, the lowering obtained from the Mating Factor α pro-peptide variant of the present invention.

DESCRIPTION

Figure 1:
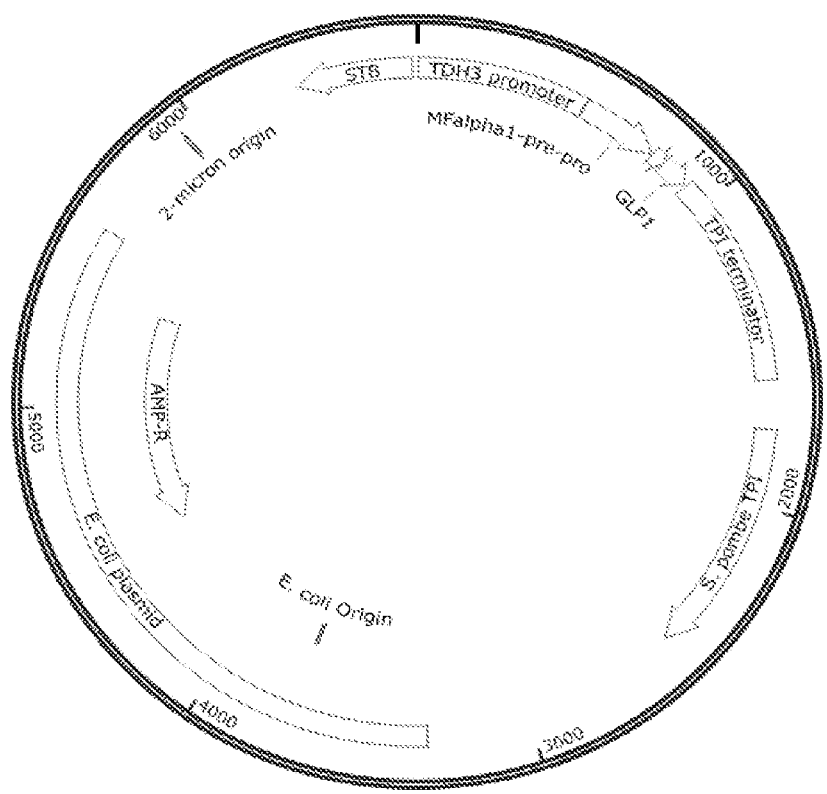
FIG. 1 shows the minimal expression plasmid as used in Example 1.

According to a first aspect of the invention there is provided a method for recombinant expression of a polypeptide in yeast comprising the culturing of a yeast strain comprising a DNA sequence encoding a processing and secretion signal upstream of the polypeptide, wherein said processing and secretion signal comprises a Mating Factor α pro-peptide variant having at least one substitution in the VIGYL (SEQ ID NO:3) sequence at positions 38-42 to comprise the amino acid sequence of the general formula (I):

$$X_{38}-X_{39}-X_{40}-X_{41}-X_{42} \quad (I) \quad (\text{SEQ ID NO: 1})$$

wherein
- $X_{38}$ is F, L, I or V;
- $X_{39}$ L, I, V or M;
- $X_{40}$ is A, G, S, E, Q, Y, F, W, R, K, H, L, I, V or M;
- $X_{41}$ is S, Y, F, W, L, I, V or M;
- $X_{42}$ is Y, W, L, I, V, M or S;
- with the proviso that $X_{38}$-$X_{42}$ is not VIGYS (SEQ ID NO:4).

The term "leader sequence" as used herein is intended to mean an amino acid sequence consisting of a pre-peptide (the signal peptide) and a pro-peptide. Non-limiting examples of leader sequences are e.g. the alpha-factor signal leader from *S. cerevisiae* and the synthetic leader sequences for yeast described in WO95/34666.

"Pre-peptide" as used herein is intended to mean a signal peptide which is present as an N-terminal sequence on the precursor form of a polypeptide to be expressed. The function of the signal peptide is to facilitate translocation of the polypeptide into the endoplasmic reticulum in the host cell. The signal peptide is normally cleaved off in the course of this process. The signal peptide may be heterologous or homologous to the host cell producing the polypeptide.

"Pro-peptide" as used herein is intended to mean a peptide sequence whose function is to allow the expressed polypeptide to be directed from the endoplasmic reticulum to the Golgi apparatus and further to a secretory vesicle for secretion into the culture medium (i.e. exportation of the polypeptide across the cell wall or at least through the cellular membrane into the periplasmic space of the yeast cell). Non-limiting examples of a pro-peptide are the yeast α-factor pro-peptide (vide U.S. Pat. Nos. 4,546,082 and 4,870,008) and the synthetic pro-peptides disclosed in U.S. Pat. Nos. 5,395,922; 5,795,746; 5,162,498 and WO 98/32867. The pro-peptide will preferably contain an endopeptidase processing site at the C-terminal end, such as a Lys-Arg sequence or any functional analog thereof.

The term "Mating Factor α" (MFα, MFa or MFalpha) as used herein is intended to mean the *Saccharomyces cerevisiae* prepro-sequence, comprising the Mating Factor α pre-peptide as amino acid residues 1-19 and Mating Factor α pro-peptide as amino acid residues 20-85 in the structure:

```
                                              (SEQ ID NO: 2)
MRFPSIFTAVLFAASSALAAPVNTTTEDETAQIPAEAVIGYLDLEGDFDV

AVLPFSNSTNNGLLFINTTIASIAAKEEGVSLDKR.
```

The Mating Factor α comprises the sequence VIGYL (SEQ ID NO:3) as amino acid residues 38-42. A variant of Mating Factor α has been used for recombinant expression of polypeptides which comprises the sequence VIGYS (SEQ ID NO:4) as amino acid residues 38-42 in the Mating Factor α sequence.

In the present context the terms "polypeptide", "protein" and "peptide" may be used interchangeably to designate a polypeptide. It is to be understood that the particular term used has no limitation as to the size of the molecule (unless directly stated in the particular context).

Amino acid residues are generally designated according to single letter abbreviation according to IUPAC nomenclature, e.g. D meaning aspartic acid (Asp) and G meaning glycine. However, in some instances the corresponding three letter abbreviation is also used.

"Genetically encoded amino acids" as used herein is intended to mean the the group consisting of the following amino acids: G, P, A, V, L, I, M, C, F, Y, W, H, K, R, Q, N, E, D, S, T as well as any biological modification hereof. Non-limiting examples of such biological modifications are e.g. amidation, glycosylation and disulphide bond formation.

"Analogues" as used herein is intended to mean polypeptides which are derived from the reference polypeptide by means of substitution, deletion and/or addition of one or more amino acid residues from the polypeptide. Non-limiting examples of an analogue of GLP-1(7-37) (SEQ ID NO:5) are GLP-1(7-37)[K34R] (SEQ ID NO: 6) where residue 34 has been substituted by an arginine residue and GLP-1(9-37)[K34R] (SEQ ID NO: 7) where residue 34 has been substituted with an arginine residue and amino acid residues 7-8 have been deleted (using the common numbering of amino acid residues for GLP-1 peptides).

"Variant" as used herein with reference to a polypeptide is intended to mean a chemical variant of the polypeptide which retains substantially the same main function as the original protein. Hence a variant is typically a modified version of a polypeptide wherein as few modifications are introduced as necessary for the modified polypeptide to have some desirable property while preserving substantially the same main function of the original polypeptide. Non-limiting examples of polypeptide variants are e.g. extended polypeptides, truncated polypeptides, fusion polypeptides and analogues. A non-limiting example of a variant of Mating Factor α pro-peptide is L42S-Mating Factor α (20-85) (SEQ ID NO:8). A non-limiting example of a variant of GLP-1(7-37) is GLP-1(7-37)[K34R].

In one embodiment, a variant of a polypeptide comprises from 1-2 amino acid substitutions, deletions or additions as compared to the unmodified polypeptide. In another embodiment, a variant comprises from 1-5 amino acid substitutions, deletions or additions as compared to the unmodified polypeptide. In another embodiment, a variant comprises from 1-15 amino acid substitution, deletion or additions relative to the corresponding unmodified polypeptide.

According to a second aspect of the invention there is provided a Mating Factor α pro-peptide variant having at least one substitution in the VIGYL (SEQ ID NO:3) sequence at positions 38-42 to comprise the amino acid sequence of the general formula (I):

$$\text{(I)}$$
$$\text{(SEQ ID NO: 1)}$$
$$X_{38}\text{-}X_{39}\text{-}X_{40}\text{-}X_{41}\text{-}X_{42}$$

wherein
$X_{38}$ is F, L, I or V;
$X_{39}$ L, I, V or M;
$X_{40}$ is A, G, S, E, Q, Y, F, W, R, K, H, L, I, V or M;
$X_{41}$ is S, Y, F, W, L, I, V or M;
$X_{42}$ is Y, W, L, I, V, M or S;
with the proviso that $X_{38}$-$X_{42}$ is not VIGYS (SEQ ID NO:4). In one embodiment the Mating Factor α pro-peptide variant does not comprise VIGYS (SEQ ID NO:4), VIDYS (SEQ ID NO:45), VATYL (SEQ ID NO:46), VIGYR (SEQ ID NO:47), or AIGYL (SEQ ID NO:48) as $X_{38}$-$X_{42}$.

According to a third aspect of the invention there is provided a GLP-1 precursor which is a fusion polypeptide comprising:
A pre-peptide,
A Mating Factor α pro-peptide variant having at least one substitution in the VIGYL (SEQ ID NO:3) sequence at positions 38-42 to comprise the amino acid sequence of the general formula (I):

$$\text{(I)}$$
$$\text{(SEQ ID NO: 1)}$$
$$X_{38}\text{-}X_{39}\text{-}X_{40}\text{-}X_{41}\text{-}X_{42}$$

wherein
$X_{38}$ is F, L, I or V;
$X_{39}$ L, I, V or M;
$X_{40}$ is A, G, S, E, Q, Y, F, W, R, K, H, L, I, V or M;
$X_{41}$ is S, Y, F, W, L, I, V or M;
$X_{42}$ is Y, W, L, I, V, M or S;
with the proviso that $X_{38}$-$X_{42}$ is not VIGYS (SEQ ID NO:4),
Optionally an extension peptide, and
A GLP-1 peptide.

The term "GLP-1 peptide", as used herein, is intended to designate GLP-1 (7-37), GLP-1 (7-36) amide as well as analogues thereof, which are capable of being produced by conventional recombinant DNA techniques as well as conventional synthetic methods. Such GLP-1 peptides include but are not limited to native glucagon-like peptide-1, for instance such peptide fragments which comprises GLP-1 (7-37) and functional variants thereof as disclosed in WO 87/06941; such peptide fragments which comprise GLP-1 (7-36) and functional derivatives thereof as disclosed in WO 90/11296; such analogues of the active GLP-1 peptides 7-34, 7-35, 7-36, and 7-37 as disclosed in WO 91/11457; such N-terminal truncated fragments of GLP-1 as disclosed in EP 0699686-A2; and such GLP-1 analogues and derivatives that include an N-terminal imidazole group as disclosed in EP 0708179-A2. Non-limiting examples of a GLP-1 peptide is GLP-1(7-37) and GLP-1(7-37)[K34R].

The term "GLP-1 precursor" as used herein is intended to mean a polypeptide comprising an extended GLP-1 peptide where the extension serves to facilitate the secretion, expression or recovery of the GLP-1 peptide. Examples of GLP-1 precursors may be found in WO03/010186 and WO09/083549. GLP-1 precursors are intended to include GLP-1 peptides having a small extension, e.g. 2-5 amino acid residues, as well as GLP-1 peptides having longer extensions comprising a pre-peptide and a pro-peptide.

In one embodiment of the method for recombinant expression of a polypeptide in yeast said amino acid sequence of the general formula (I) has a sequence wherein
$X_{38}$ is F, L or V;
$X_{39}$ L, I, V or M;
$X_{40}$ is G or R;
$X_{41}$ is S, Y, L, I, V or M, and
$X_{42}$ is Y, W, L, V or M.

In another embodiment said amino acid sequence of the general formula (I) has a sequence wherein
$X_{38}$ is I or V;
$X_{39}$ L, I, V or M;
$X_{40}$ is A, G, S, E, Q, Y, F, W, R, K, H, L, I, V or M;
$X_{41}$ is Y, F, or W, and
$X_{42}$ is L or I.

In another embodiment said amino acid sequence of the general formula (I) has a sequence wherein
$X_{38}$ is V;
$X_{39}$ L, I, V or M;
$X_{40}$ is G or R;
$X_{41}$ is Y, and
$X_{42}$ is L.

In another embodiment said amino acid sequence of the general formula (I) has a sequence wherein $X_{40}$ is R. In another embodiment said amino acid sequence of the general formula (I) has a sequence wherein $X_{40}$ is R and $X_{42}$ is L.

In yet another embodiment said amino acid sequence of the general formula (I) has a sequence wherein $X_{38}$ is V, $X_{39}$ is I, $X_{40}$ is R, $X_{41}$ is Y and $X_{42}$ is L.

In another embodiment the polypeptide being recombinantly expressed is a GLP-1 peptide or a variant thereof, such as GLP-1(7-37)[K34R] or GLP-1(9-37)[K34R].

In one embodiment the polypeptide being recombinantly expressed has an N-terminal extension, i.e. positioned between the Mating Factor α variant and the polypeptide to be manufactured. This extension may facilitate the expression or secretion of the polypeptide from the host cell, or it may protect part of the polypeptide from undesirable proteolytical processing in the N-terminal. In another embodiment the N-terminal extension is a polypeptide having from 2-10 amino acid residues or having from about 8 to about 200 amino acid residues. Smaller N-terminal extensions are often used when the extension serves to facilitate the expression of the polypeptide in a host cell, or when the extension serves to protect a polypeptide from being proteolytically processed in the N-terminal. In another embodiment the N-terminal extension is selected from the group consisting of EEK, EEAEK (SEQ ID NO:9), HK, EEAHK (SEQ ID NO:10), E(EA)2HK (SEQ ID NO:11), E(EA)3HK (SEQ ID NO:12), EEGHK (SEQ ID NO:13), EHPK, EEGEPK (SEQ ID NO:14), EEAHELK (SEQ ID NO:15), EEAHEVK (SEQ ID NO:16), EEAHEMK (SEQ ID NO:17), EEAHEFK (SEQ ID NO:18), EEAHEYK (SEQ ID NO:19), EEAHEWKEEGNTTPK (SEQ ID NO:20) and EELDARLEALK (SEQ ID NO:21). In another embodiment the N-terminal extension is selected from the group consisting of QPMYKR (SEQ ID NO:22), GQPMYK (SEQ ID NO:23), PGQPMY (SEQ ID NO:24), KPGQPM (SEQ ID NO:25), LKPGQP (SEQ ID NO:26), QLKPGQ (SEQ ID NO:27), LQLKPG (SEQ ID NO:28), WLQLKP (SEQ ID NO:29), HWLQLK (SEQ ID NO:30), WHWLQL (SEQ ID NO:31), AWHWLQ (SEQ ID NO:32), EAWHWL (SEQ ID NO:33), AEAWHW (SEQ ID NO:34) and EAEAWH (SEQ ID NO:35).

When the expressed polypeptide includes an N-terminal extension, it is customary to cleave off this N-terminal extension by the use of a protease, a peptidase or by chemical cleavage. Proteases such as trypsin, *Acromobacter lyticus* protease and Enterokinase may be used. The particular proteolytic enzyme selected for the cleavage is often determined by the polypeptide being manufactured. Hence, the person skilled in the art will often select the proteolytic enzyme based on the polypeptides sequence, specifically the presence of any internal primary or secondary cleavage sites, as well as adapting the N-terminal extension to form a good cleavage site.

The cleavage efficiency of a protease when used to cleave a polypeptide expressed with an N-terminal extension may be determined by a simple assay as follows: A suitable aqueous solution of the polypeptide is incubated at a pH and temperature which is favourable to the protease and samples are withdrawn from the reaction mixture over time. As soon as the samples are withdrawn the enzyme activity is inactivated. After collecting all the samples covering the timespan of interest, the concentration of the corresponding polypeptide without the N-terminal extension is determined by e.g. HPLC analysis. Depicting the concentration of the cleaved polypeptide as a function of time will indicate the progress of the reaction. Comparing such reaction traces for different N-terminal extension of the polypeptide will allow a ranking of the N-terminal extensions in accordance with the ability of the protease to liberate the polypeptide without N-terminal extension.

The nucleic acid construct encoding the polypeptide may suitably be of genomic, cDNA or synthetic origin. Amino acid sequence alterations are accomplished by modification of the genetic code by well known techniques.

The DNA sequence encoding the polypeptide are usually inserted into a recombinant vector which may be any vector, which may conveniently be subjected to recombinant DNA procedures, and the choice of vector will often depend on the host cell into which it is to be introduced. Thus, the vector may be an autonomously replicating vector, i.e. a vector, which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the polypeptide is operably linked to additional segments required for transcription of the DNA. The term, "operably linked" indicates that the segments are arranged so that they function in concert for their intended purposes, e.g. transcription initiates in a promoter and proceeds through the DNA sequence coding for the polypeptide until it terminates within a terminator.

Thus, expression vectors for use in expressing the polypeptide will comprise a promoter capable of initiating and directing the transcription of a cloned gene or cDNA. The promoter may be any DNA sequence, which shows transcriptional activity in the host cell of choice and may be derived from genes encoding proteins either homologous or heterologous to the host cell.

Additionally, expression vectors for use of expression of the polypeptide will also comprise a terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Expression of the polypeptide is aimed for being directed into the secretory pathway for extracellular expression into the growth medium. Useful signal peptides for use as the pre-peptide in leaders for expression in yeast host cells are obtained e.g. from the genes for *Saccharomyces cerevisiae* alpha-factor and *Saccharomyces cerevisiae* invertase. Other examples of useful pre-peptides (signal peptides) are the yeast aspartic protease 3 (Yps1) signal peptide (Egel-Mitani et al. (1990) YEAST 6:127-137 and U.S. Pat. No. 5,726,038), the alpha-factor signal of the MFα1 gene (Thorner (1981) in The Molecular Biology of the Yeast *Saccharomyces cerevisiae*, Strathern et al., eds., pp 143-180, Cold Spring Harbor Laboratory, N.Y.) and U.S. Pat. No. 4,870,008), the signal peptide of mouse salivary amylase (O. Hagenbuchle et al., Nature 289, 1981, pp. 643-646), a modified carboxypeptidase signal peptide (L. A. Valls et al., Cell 48, 1987, pp. 887-897) and the yeast BAR1 signal peptide (WO 87/02670).

The procedures used to ligate the DNA sequences coding for the polypeptide, the promoter, the terminator and secretory signal sequence, respectively, and to insert them into suitable vectors containing the information necessary for replication, are well known to persons skilled in the art (cf., for instance, Sambrook et al., Molecular Cloning: A Laboratory Manual, Cold Spring Harbor, New York, 1989).

Many yeast cells contain an endogenous plasmid, called the 2 micron plasmid that contains various elements that ensure its stable maintenance in the yeast cell (Guerineau et al., 1971, Biochem. Biophys. Res. Comm. 42(3):550-557). The whole or part of this endogenous 2 micron can be used in conjunction with a recombinant gene, as a method for securing stable maintenance of the sequences necessary for the recombinant expression (Beggs J. D., 1978, Transformation of yeast by a replicating hybrid plasmid, Nature, 275:104-109). It has been found by the present inventor that when the endogenous 2 micron plasmid is present in the cell, the expression plasmid for recombinant expression only needs to comprise the replication origin and the STB region. The other factors present on the endogenous 2 micron plasmid can function in trans. The replication origin and the STB region only constitute a small part of the endogenous 2μ plasmid.

In an aspect the present invention provides an expression plasmid containing only the replication origin and the STB region from the 2 micron plasmid. Hence, this minimal expression plasmid does not contain any of the FLP region, the repeat 1 region, the REP1 region, D-protein, repeat 2 region and REP2 region. In an embodiment this plasmid comprises an expression cassette, an *E. coli* part including an AmpR gene, an *S. pombe* sequence encoding triose-phosphate-isomerase as described in Russell, P R (1985, Transcription of the triose-phosphate gene of *Schizosaccharomyces pombe* initiates from a start point different from that in *Saccharomyces cerevisiae*, Gene, 40:125-130). In another embodiment the minimal plasmid comprises no AmpR or other antibiotic resistance gene. Such an antibiotic resistance gene is useful during the cloning work in e.g. *E. coli* but it is preferable to eliminate the antibiotic resistance gene in the plasmid used for industrial scale recombinant protein expression. The antibiotic resistance gene can be made non-functional or removed from the host cell by well known procedures, see e.g. WO 00/04172. The minimal expression plasmid is useful for expression of a polypeptide in a yeast.

The vectors of the present invention preferably contain one or more selectable markers which permit easy selection of transformed cells. A selectable marker is a gene the product of which provides for biocide or viral resistance, resistance to heavy metals, complement auxotrophies, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Selectable markers for use in auxotroph yeast cells include ADE2, HIS3, LEU2, LYS2, MET3, TRP1, and URA3. A preferred selectable marker for yeast is the *Schizosaccharomyces pombe* TPI gene (Russell (1985) Gene 40:125-130).

In the vector, the polynucleotide sequence is operably connected to a suitable promoter sequence. The promoter may be any nucleic acid sequence which shows transcriptional activity in the host cell of choice including mutant, truncated, and hybrid promoters, and may be obtained from genes encoding extra-cellular or intra-cellular polypeptides either homologous or heterologous to the host cell. Examples of useful promoters in yeast host cells are the *Saccharomyces cerevisiae* MFα1, TPI1, ADH2, TDH3 or PGK1 promoters.

The polynucleotide construct of the invention will also typically be operably connected to a suitable terminator. In yeast an example of a suitable terminator is the TPI1 terminator (Alber et al. (1982) J. Mol. Appl. Genet. 1:419-434), but could be any endogenous yeast terminator.

The procedures used to ligate the polynucleotide sequence of the invention, the promoter and the terminator, respectively, and to insert them into suitable yeast vectors containing the information necessary for yeast replication, are well known to persons skilled in the art. It will be understood that the vector may be constructed either by first preparing a DNA construct containing the entire DNA sequence encoding the polypeptide to be expressed, and subsequently inserting this fragment into a suitable expression vector, or by sequentially inserting DNA fragments containing genetic information for the individual elements (such as the Mating Factor α variant of the invention, the polypeptide to be expressed optionally including a N-terminal extension) followed by assembly of the elements by ligation, seamless cloning methods or by cloning directly in the yeast cell by homologous recombination.

The present invention also relates to recombinant host cells, comprising a polynucleotide sequence encoding the Mating Factor α variant of the invention and the polypeptide to be expressed. A vector comprising such polynucleotide sequence is introduced into the host cell so that the vector is maintained as a chromosomal integrant or as a self-replicating extra-chromosomal vector.

"Host cell" as used herein is intended to mean a microorganism which is used for the expression of a polypeptide of interest. A host cell encompasses any progeny of a parent cell that is not identical to the parent cell due to mutations that occur during replication.

A suitable host cell for the present invention is a yeast cell. "Yeast" as used herein includes ascosporogenous yeast (Endomycetales), basidiosporogenous yeast, and yeast belonging to the Fungi Imperfecti (Blastomycetes). The ascosporogenous yeasts are divided into the families Spermophthoraceae and Saccharomycetaceae. The latter is comprised of four subfamilies, Schizosaccharomycoideae (e.g., genus *Schizosaccharomyces*), Nadsonioideae, Lipomycoideae, and Saccharomycoideae (e.g., genera *Pichia, Kluyveromyces* and *Saccharomyces*). The basidiosporogenous yeasts include the genera *Leucosporidim, Rhodosporidium, Sporidiobolus, Filobasidium*, and *Filobasidiella*. Yeast belonging to the Fungi Imperfecti are divided into two families, Sporobolomycetaceae (e.g., genera *Sorobolomyces* and *Bullera*) and Cryptococcaceae (e.g., genus *Candida*).

Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980. The biology of yeast and manipulation of yeast genetics are well known in the art (see, e.g., *Biochemistry and Genetics of Yeast*, Bacil, M., Horecker, B. J., and Stopani, A. O. M., editors, 2nd edition, 1987; The Yeasts, Rose, A. H., and Harrison, J. S., editors, 2nd edition, 1987; and *The Molecular Biology of the Yeast Saccharomyces*, Strathern et al., editors, 1981).

The yeast host cell used in the process of the invention may be any suitable yeast organism which, on cultivation, produces large amounts of the polypeptide to be expressed.

Examples of suitable yeast organisms are strains selected from a cell of a species of *Candida, Kluyveromyces, Saccharomyces, Schizosaccharomyces, Pichia, Hansenula,* and *Yarrowia*. In one embodiment, the yeast host cell is selected from a *Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis, Schizosaccharomyces pombe, Sacchoromyces uvarum, Pichia kluyveri, Yarrowia Candida utilis, Candida cacaoi,* and *Geotrichum fermentans*. Other useful yeast host cells are a *Kluyveromyces lactis, Kluyveromyces fragilis, Hansenula polymorpha, Pichia pastoris Yarrowia lipolytica, Schizosaccharomyces pombe, Ustilgo maylis, Candida maltose, Pichia guillermondii* and *Pichia methanoliol* (cf. Gleeson et al., J. Gen. Microbiol. 132, 1986, pp. 3459-3465; U.S. Pat. Nos. 4,882,279 and 4,879,231). The transformation of the yeast cells may for instance be effected by protoplast formation followed by transformation in a manner known per se.

The host cell for expressing the polypeptide is preferably a cell free from any functional antibiotic resistance genes. Although such antibiotic resistance genes are useful during initial cloning steps in e.g. *E. coli*, the antibiotic resistance genes can be made non-functional or removed from the host cell by well known procedures, see e.g. WO 00/04172.

"Medium" as used herein is intended to mean a liquid solution for cultivating the host cell, i.e. supporting the growth and product formation of the yeast. A suitable medium for yeast is e.g. YPD or as described in WO2008/037735. The medium contains at least one carbon source, one or several nitrogen sources, essential salts including salts of potassium, sodium, magnesium, phosphate and sulphate, trace metals, water soluble vitamins, and process aids including but not limited to antifoam agents, protease inhibitors, stabilizers, ligands and inducers. Typical carbon sources are e.g. mono- or disaccharides. Typical nitrogen sources are, e.g. ammonia, urea, amino acids, yeast extract, corn steep liquor and fully or partially hydrolysed proteins. Typical trace metals are e.g. Fe, Zn, Mn, Cu, Mo and $H_3BO_3$. Typical water soluble vitamins are e.g. biotin, pantothenate, niacin, thiamine, p-aminobenzoic acid, choline, pyridoxine, folic acid, riboflavin and ascorbic acid.

By "fermentation" as used herein is intended to mean an aseptic process used for propagating microorganisms submerged in a liquid medium. The fermentation is preferably carried out in aseptic, stirred tanks with supply lines for addition of compressed, sterile gasses consisting of but not limited to air, oxygen and ammonia. A fermentation tank can contain sensors and devices for monitoring pH, temperature, pressure, agitation rate, dissolved oxygen level, liquid content, foam level, feed addition rates and rates of adding acid and base. Furthermore, the fermentation tank can be equipped with optical devices for monitoring levels of cell density, concentrations of metabolites and products regardless of their physio-chemical form.

The desired product produced during the fermentation is present as soluble extracellular material or as intracellular material either in the form of soluble material or as insoluble material including aggregated material. It is preferable that it is present as soluble extracellular material. A fermentation process is typically carried out in tanks with a working volume ranging from 100 mL to 200.000 L. A fermentation process can be operated as a batch process, a fed-batch process, a repeated fed-batch process or a continuous process.

The secreted polypeptides, a significant proportion of which will be present in the medium in correctly processed form, may be recovered from the medium by conventional procedures including separating the yeast cells from the medium by centrifugation, filtration or catching the polypeptide by an ion-exchange matrix or by a reverse phase absorption matrix, precipitating the protein components of the supernatant or filtrate by means of a salt, e.g. ammonium sulphate, followed by purification by a variety of chromatographic procedures, e.g. ion exchange chromatography, affinity chromatography, or the like.

The novel Mating Factor α variants of the present invention also facilitate reduced O-glycosylation of the polypeptide during expression in yeast. As such the Mating Factor α variants of the present invention can be used in an improved method for making polypeptides such as GLP-1 peptides in yeast. Expressing the polypeptide in a yeast cell having reduced capacity for O-glycosylation may maintain the improved yield of said precursor while at the same time reducing even further the fraction of said polypeptide that is O-glycosylated during expression.

Protein O-mannosyltransferases (PMTs) initiate the assembly of O-mannosyl glycans, an essential protein modification in fungi. PMTs are conserved in fungi and the PMT family is phylogenetically classified into PMT1, PMT2 and PMT4 subfamilies, which differ in protein substrate specificity. The protein O-mannosyltransferases Pmt1p and Pmt2p are catalyzing the O-glycosylation of serine and threonine residues in proteins in the endoplasmic reticulum of yeast by transfer of a mannosyl residue from Dolichyl phosphate-D-mannose (Gentzsch et al., FEBS Lett 1995, 18, pp 128-130). In *Saccharomyces cerevisiae* as well as in many other yeasts the PMT family is highly redundant, and only the simultaneous deletion of PMT1/PMT2 and PMT4 subfamily members is lethal (Girrbach and Strahl, J. Biol. Chem. 2003, 278, pp 12554-62). U.S. Pat. No. 5,714,377 describe that yeast cells having reduced O-glycosylation capacity from PMT1/PMT2 modification are still viable and show good growth characteristics in industrial fermentation conditions.

Non-Limiting Embodiments

The invention is further described by the following non-limiting embodiments:
1. A method for recombinant expression of a polypeptide in yeast comprising the culturing of a yeast strain comprising a DNA sequence encoding a processing and secretion signal upstream of the polypeptide, wherein said processing and secretion signal comprises a Mating Factor α pro-peptide variant having at least one substitution in the VIGYL (SEQ ID NO:3) sequence at positions 38-42 to comprise the amino acid sequence of the general formula (I):

$$X_{38}\text{-}X_{39}\text{-}X_{40}\text{-}X_{41}\text{-}X_{42} \quad \text{(I) (SEQ ID NO: 1)}$$

wherein
- $X_{38}$ is F, L, I or V;
- $X_{39}$ L, I, V or M;
- $X_{40}$ is A, G, S, E, Q, Y, F, W, R, K, H, L, I, V or M;
- $X_{41}$ is S, Y, F, W, L, I, V or M;
- $X_{42}$ is Y, W, L, I, V, M or S;
- with the proviso that $X_{38}\text{-}X_{42}$ is not VIGYS (SEQ ID NO:4).

2. The method according to embodiment 1 wherein
- $X_{38}$ is F, L or V;
- $X_{39}$ L, I, V or M;
- $X_{40}$ is G or R;
- $X_{41}$ is S, Y, L, I, V or M, and
- $X_{42}$ is Y, W, L, V or M.

3. The method according to claim 1 wherein
- $X_{38}$ is I or V;
- $X_{39}$ L, I, V or M;
- $X_{40}$ is A, G, S, E, Q, Y, F, W, R, K, H, L, I, V or M;
- $X_{41}$ is Y, F, or W, and
- $X_{42}$ is L or I.

4. The method according to any of embodiments 1-3 wherein
- $X_{38}$ is V;
- $X_{39}$ L, I, V or M;
- $X_{40}$ is G or R;
- $X_{41}$ is Y, and
- $X_{42}$ is L.

5. The method according to any of embodiments 1-4, wherein four of the amino acid residues in $X_{38}\text{-}X_{39}\text{-}X_{40}\text{-}X_{41}\text{-}X_{42}$ are identical to the corresponding amino acid residue in VIGYL  (SEQ ID NO: 3)
or
VIGYS. (SEQ ID NO: 4)

6. The method according to any of embodiments 1-5, wherein at least three of the amino acid residues in $X_{38}\text{-}X_{39}\text{-}X_{40}\text{-}X_{41}\text{-}X_{42}$ are identical to the corresponding amino acid residue in VIGYL (SEQ ID NO:3) or VIGYS (SEQ ID NO:4).

7. The method according to any of embodiments 1-6, wherein $X_{41}$ is Y.

8. The method according to any of embodiments 1-6, wherein $X_{41}$ is L.

9. The method according to any of embodiments 1-8, wherein $X_{42}$ is L.

10. The method according to any of embodiments 1 and 5-8, wherein $X_{42}$ is S.

11. The method according to any of embodiments 1 and 5-8, wherein $X_{42}$ is Y, W, L, I, V or M.

12. The method according to any of embodiments 1-11, wherein $X_{40}$ is R.

13. The method according to embodiment 12, wherein $X_{38}$ is V, $X_{39}$ is I, $X_{41}$ is Y and $X_{42}$ is L.

14. The method according to embodiment 12, wherein $X_{38}$ is V, $X_{39}$ is I, $X_{41}$ is Y and $X_{42}$ is S.

15. The method according to any of embodiments 1 and 12, wherein formula (I) is VI-$X_{40}$-YL or VI-$X_{40}$-YS.

16. The method according to embodiment 15 wherein $X_{40}$ is A, Y, F, W, R, K, L, I, V or M.

17. The method according to any of embodiments 1-16, wherein said Mating Factor α pro-peptide variant has less than 10 amino acid residue changes outside of the $X_{38}\text{-}X_{42}$ sequence as compared to the Mating Factor α pro-peptide as set out in SEQ ID NO:2 (amino acid residues 20-85).

18. The method according to any of embodiments 1-17, wherein said Mating Factor α pro-peptide variant has less than 5 amino acid residue changes outside of the $X_{38}\text{-}X_{42}$ sequence as compared to the Mating Factor α pro-peptide as set out in SEQ ID NO:2 (amino acid residues 20-85).

19. The method according to any of embodiments 1-18, wherein said Mating Factor α pro-peptide variant has less than 2 amino acid residue changes outside of the $X_{38}\text{-}X_{42}$ sequence as compared to the Mating Factor α pro-peptide as set out in SEQ ID NO:2 (amino acid residues 20-85).

20. The method according to any of embodiments 1-19, wherein said Mating Factor α pro-peptide variant is part of a Mating Factor α prepro-peptide comprising a pre-peptide as the N-terminal part fused to said Mating Factor α pro-peptide variant as the C-terminal part.

21. The method according to embodiment 20, wherein said pre-peptide is from yeast aspartic protease 3 (YAP3) signal peptide, from the α-factor signal of the MFα1 gene from *S. cerevisiae* or a variant thereof.

22. The method according to any of embodiments 1-21, wherein said yeast carries at least one genetic modification reducing its capacity for O-glycosylation.

23. The method according to embodiment 22, wherein said yeast carries at least one genetic modification within the genes for PMT1 or PMT2 reducing its capacity for O-glycosylation.

24. The method according to any of embodiments 22-23, wherein said yeast carries at least one genetic modification reducing its capacity for O-glycosylation by the protein O-mannosyltransferase 1 (PMT1) of the polypeptide GLP-1(7-37)[K34R] when expressed with the alpha leader as compared to the yeast carrying the corresponding unmodified genes.

25. The method according to any of embodiments 22-24, wherein said yeast carries at least one genetic modification reducing its capacity for O-glycosylation by protein O-mannosyltransferase 2 (PMT2) of the polypeptide GLP-1(7-37)[K34R] when expressed with the alpha leader as compared to the yeast carrying the corresponding unmodified genes.

26. The method according to any of embodiments 22-25, wherein said capacity for O-glycosylation is reduced by at least a factor 2.

27. The method according to any of embodiments 22-26, wherein said capacity for O-glycosylation is reduced by at least a factor 4.

28. The method according to any of embodiments 22-27, wherein said at least one genetic modification is located in the coding region of PMT1 or PMT2.

29. The method according to any of embodiments 22-27, wherein said at least one genetic modification is located in the regions responsible for or involved in the expression and/or transcriptional regulation of PMT1 or PMT2.
30. The method according to any of embodiments 22-27, wherein the PMT1 gene in said yeast is deleted.
31. The method according to any of embodiments 22-27, wherein the PMT1 and PMT2 genes in said yeast are both deleted.
32. The method according to any of embodiments 1-31, wherein said polypeptide comprises a GLP-1 peptide.
33. The method according to embodiment 32, wherein said polypeptide comprises GLP-1(9-37)[K34R] or GLP-1(9-37)[K34R].
34. The method according to embodiment 33, wherein said polypeptide is GLP-1(7-37)[K34R], GLP-1(9-37)[K34R] or GLP-1(9-37)[K34R,G37K] (SEQ ID NO:43).
35. The method according to any of embodiments 32-34, wherein said polypeptide has an N-terminal extension.
36. The method according to embodiment 35, wherein said N-terminal extension is selected from the group consisting of EEK, EEAEK (SEQ ID NO:9), HK, EEAHK (SEQ ID NO:10), E(EA)2HK (SEQ ID NO:11), E(EA)3HK (SEQ ID NO:12), EEGHK (SEQ ID NO:13), EHPK, EEGEPK (SEQ ID NO:14), EEAHELK (SEQ ID NO:15), EEAHEVK (SEQ ID NO:16), EEAHEMK (SEQ ID NO:17), EEAHEFK (SEQ ID NO:18), EEAHEYK (SEQ ID NO:19), EEAHEWKEEGNTTPK (SEQ ID NO:20) and EELDARLEALK (SEQ ID NO:21).
37. The method according to embodiment 35, wherein said N-terminal extension is selected from the group consisting of DV, DVKPGQPLA (SEQ ID NO:36), DVKPGQPEY (SEQ ID NO:37), DVKPGEPLY (SEQ ID NO:38), DVKPGQPLY (SEQ ID NO:39), DVKPGQPLE (SEQ ID NO:40), DVKPGQPMY (SEQ ID NO:41) and DVKPGQPMYDDDDK (SEQ ID NO:42).
38. The method according to embodiment 35, wherein said N-terminal extension is selected from the group consisting of QPMYKR (SEQ ID NO:22), GQPMYK (SEQ ID NO:23), PGQPMY (SEQ ID NO:24), KPGQPM (SEQ ID NO:25), LKPGQP (SEQ ID NO:26), QLKPGQ (SEQ ID NO:27), LQLKPG (SEQ ID NO:28), WLQLKP (SEQ ID NO:29), HWLQLK (SEQ ID NO:30), WHWLQL (SEQ ID NO:31), AWHWLQ (SEQ ID NO:32), EAWHWL (SEQ ID NO:33), AEAWHW (SEQ ID NO:34) and EAEAWH (SEQ ID NO:35).
39. Mating Factor α pro-peptide variant having at least one substitution in the VIGYL (SEQ ID NO:3) sequence at positions 38-42 to comprise the amino acid sequence of the general formula (I):

(I)
(SEQ ID NO: 1)
$X_{38}-X_{39}-X_{40}-X_{41}-X_{42}$ wherein
$X_{38}$ is F, L, I or V;
$X_{39}$ L, I, V or M;
$X_{40}$ is A, G, S, E, Q, Y, F, W, R, K, H, L, I, V or M;
$X_{41}$ is S, Y, F, W, L, I, V or M;
$X_{42}$ is Y, W, L, I, V, M or S;
with the proviso that $X_{38}-X_{42}$ is not VIGYS (SEQ ID NO:4).

40. The Mating Factor α pro-peptide variant according to embodiment 39 wherein $X_{38}-X_{42}$ is not VIGYS (SEQ ID NO:4), VIDYS (SEQ ID NO:45), VATYL (SEQ ID NO:46), VIGYR (SEQ ID NO:47), or AIGYL (SEQ ID NO:48).
41. GLP-1 precursor which is a fusion polypeptide comprising:
A pre-peptide,
A Mating Factor α pro-peptide variant having at least one substitution in the VIGYL (SEQ ID NO:3) sequence at positions 38-42 to comprise the amino acid sequence of the general formula (I):

(I)
(SEQ ID NO: 1)
$X_{38}-X_{39}-X_{40}-X_{41}-X_{42}$ wherein
$X_{38}$ is F, L, I or V;
$X_{39}$ L, I, V or M;
$X_{40}$ is A, G, S, E, Q, Y, F, W, R, K, H, L, I, V or M;
$X_{41}$ is S, Y, F, W, L, I, V or M;
$X_{42}$ is Y, W, L, I, V, M or S;
with the proviso that $X_{38}-X_{42}$ is not VIGYS (SEQ ID NO:4),
Optionally an extension peptide, and
A GLP-1 peptide.
42. The GLP-1 precursor according to embodiment 41 wherein the peptides comprised by said GLP-1 precursor are fused according to the order in which they are listed, i.e. pre-peptide—Mating Factor α pro-peptide variant, the optional extension peptide and the GLP-1 peptide.
43. DNA sequence encoding the polypeptide according to any of embodiments 39-42.
44. Expression vector comprising a DNA sequence according to embodiment 43.
45. Expression vector according to embodiment 44, wherein said DNA sequence encoding a polypeptide to be expressed is operatively linked to an upstream promoter and a downstream terminator.
46. Host cell comprising the expression vector according to any of embodiments 44-45.
47. The host cell according to embodiment 46, which is selected from the group consisting of *Saccharomyces* spp., *Pichia* spp., *Hansenula* spp., *Arxula* spp., *Kluyveromyces* spp., *Yarrowia* spp. and *Schizosaccharomyces* spp.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law). All headings and sub-headings are used herein for convenience only and should not be construed as limiting the invention in any way. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents. This invention

EXAMPLES

Examples 1-45

We constructed a plasmid, that contains the TDH3 promoter, the gene encoding the MFalpha pre-pro-peptide, the gene encoding an N-terminal extended GLP-1 (DVKPGQP-MYDDDDK-GLP-1(7-37)[K34R]) (SEQ ID NO:44), a minimal 2 micron region for maintenance in yeast, and a selectable marker, namely the TPI gene from *S. pombe* (see FIG. 1).

Figure 2:
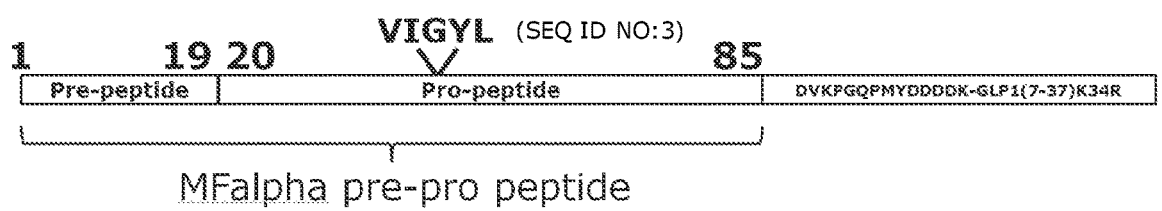
FIG. 2 shows the N-terminally extended GLP-1(7-37)[K34R] precursor including the wildtype Mating Factor α pre-pro-peptide with indication of the VIGYL (SEQ ID NO:3) subsequence of the pro-peptide.

In this plasmid background we introduced various single mutations in the region encoding position 38-42 of the MFalpha-pro-peptide region, the $X_{38}$-$X_{42}$=VIGYL (SEQ ID NO:3) sequence (see FIG. 2). The experiment using the wt VIGYL (SEQ ID NO:3) sequence is Example 1, c.f. tables 1-5. Other reference experiments are Examples 5-6, 10-11, 28-29, 37-38 and 44-45.

These plasmids were introduced into a *Saccharomyces cerevisiae* strain lacking the TPI1 gene, allowing for selection of transformants harbouring the plasmid on media containing glucose as sole carbon source. Transformants were thereafter cultivated for 3 days in shake flasks in 5 ml relevant media and the cultivation supernatants were analyzed by LCMS for concentration of secreted GLP-1 peptide, and degree of O-glycosylation of the peptide. In tables 1-5 are shown the yield and O-glycosylation degree of the wild type and of the single amino acid residue mutants of the $X_{38}$-$X_{42}$ sequence (a couple of reference examples on each position being included).

TABLE 1

Data from expression of N-terminal extended GLP-1 under control of Mating Factor α propeptide mutants having a single amino acid mutation in position 38 ($X_{38}$).
Position 38

| Example | Mutation | % conc. relative to wt | % O-glyco relative to wt |
|---|---|---|---|
| 1 | Val | 100 | 100 |
| 2 | Ile | 92 | 91 |
| 3 | Phe | 107 | 103 |
| 4 | Leu | 106 | 104 |
| 5 | Asp | 33 | 277 |
| 6 | Pro | 47 | 354 |

Concentrations of N-terminal extended GLP-1 and O-glyco impurity are normalised against the data from same expression but under control of the Mating Factor α propeptide having the wildtype Val as X38.

TABLE 2

Data from expression of N-terminal extended GLP-1 under control of Mating Factor α propeptide mutants having a single amino acid mutation in position 39 ($X_{39}$).
Position 39

| Example | Mutation | % conc. relative to wt | % O-glyco relative to wt |
|---|---|---|---|
| 1 | Ile | 100 | 100 |
| 7 | Leu | 113 | 82 |
| 8 | Val | 108 | 76 |
| 9 | Met | 126 | 88 |
| 10 | Glu | 40 | 337 |
| 11 | His | 25 | 313 |

Concentrations of N-terminal extended GLP-1 and O-glyco impurity are normalised against the data from same expression but under control of the Mating Factor α propeptide having the wildtype Ile as X39.

TABLE 3

Data from expression of N-terminal extended GLP-1 under control of Mating Factor α propeptide mutants having a single amino acid mutation in position 40 ($X_{40}$).
Position 40

| Example | Mutation | % conc. relative to wt | % O-glyco relative to wt |
|---|---|---|---|
| 1 | Gly | 100 | 100 |
| 12 | Ala | 84 | 48 |
| 13 | Ser | 79 | 89 |
| 14 | Thr | 80 | 67 |
| 15 | Asp | 51 | 90 |
| 16 | Glu | 58 | 92 |
| 17 | Gln | 87 | 98 |
| 18 | Tyr | 60 | 49 |
| 19 | Phe | 50 | 23 |
| 20 | Trp | 53 | 18 |
| 21 | Arg | 106 | 14 |
| 22 | Lys | 93 | 36 |
| 23 | His | 74 | 83 |
| 24 | Leu | 42 | 13 |
| 25 | Ile | 18 | 1 |
| 26 | Val | 26 | 1 |
| 27 | Met | 60 | 36 |
| 28 | Asn | 81 | 112 |
| 29 | Pro | 46 | 253 |

Concentrations of N-terminal extended GLP-1 and O-glyco impurity are normalised against the data from same expression but under control of the Mating Factor α propeptide having the wildtype Gly as X40.

TABLE 4

Data from expression of N-terminal extended GLP-1 under control of Mating Factor α propeptide mutants having a single amino acid mutation in position 41 ($X_{41}$).
Position 41

| Example | Mutation | % conc. relative to wt | % O-glyco relative to wt |
|---|---|---|---|
| 1 | Tyr | 100 | 100 |
| 30 | Phe | 69 | 74 |
| 31 | Trp | 79 | 73 |
| 32 | Ser | 107 | 182 |
| 33 | Leu | 129 | 104 |
| 34 | Ile | 111 | 171 |
| 35 | Val | 134 | 136 |
| 36 | Met | 131 | 151 |
| 37 | Gly | 50 | 366 |
| 38 | Asp | 27 | 590 |

Concentrations of N-terminal extended GLP-1 and O-glyco impurity are normalised against the data from same expression but under control of the Mating Factor α propeptide having the wildtype Tyr as X41.

TABLE 5

Data from expression of N-terminal extended GLP-1 under control of Mating Factor α propeptide mutants having a single amino acid mutation in position 42 ($X_{42}$). Position 42

| Example | Mutation | % conc. relative to wt | % O-glyco relative to wt |
|---|---|---|---|
| 1 | Leu | 100 | 100 |
| 39 | Ile | 98 | 64 |
| 40 | Tyr | 123 | 156 |
| 41 | Trp | 116 | 163 |
| 42 | Val | 103 | 111 |
| 43 | Met | 109 | 142 |
| 44 | Asp | 19 | 525 |
| 45 | Pro | 47 | 472 |

Concentrations of N-terminal extended GLP-1 and O-glyco impurity are normalised against the data from same expression but under control of the Mating Factor α propeptide having the wildtype Leu as X42.

Example 46

A plasmid similar to those in Examples 1-45, containing the TDH3 promoter, the gene encoding the MFalpha pre-pro-peptide, the gene encoding an N-terminal extended GLP-1 (DVKPGQPMYDDDDK-GLP-1(7-37)[K34R]) (SEQ ID NO:44), a minimal 2 micron region for maintenance in yeast, and a selectable marker (FIG. 1) was transformed into two different strain backgrounds—one containing the PMT1 gene (PMT+), the other deleted for the PMT1 gene (PMT−). The PMT1 gene is encoding a protein mannosyltransferase involved in O-glycosylation.

The MFalpha pro-peptide was either wildtype (40G) or mutated (G40R). The strains were cultivated under identical conditions in continuous cultures, with a dilution rate=0.1, and pH 5.8. Samples were analyzed by HPLC to determine the concentration of GLP-1 precursor in the spent medium and by LCMS to determine the proportion of O-glycosylated GLP-1 precursor.

The results demonstrate that the effects indeed are additive.

The G40R mutation reduced O-glycosylation with more than 80%. Deletion of PMT1 reduces O-glycosylation by further more than 80%, in this case giving levels of O-glycosylation close to the detection limit. Furthermore, the G40R mutation gives a surprising increase in yield of the N-terminally extended GLP-1 as compared to the 40G wildtype version, both in PMT+ strain as well as in pmt1 deleted strain (see Table 6).

These results demonstrate that the combination of a beneficial mutation in the MFalpha propeptide, e.g. G40R, and a PMT1 deleted host strain results in an additive reduction in O-glycosylation.

TABLE 6

Normalised maximum concentration (yield) of the peptide DVKPGQPMYDDDDK-GLP-1(7-37)[K34R] (SEQ ID NO: 44) in continuous cultures when using 40R mutated MFalpha pro-peptide as compared to the corresponding wildtype 40G.

| PMT+ strain | | PMT− strain | |
|---|---|---|---|
| 40G | 40R (relative to 40G in same strain) | 40G | 40R (relative to 40G in same strain) |
| 100% | 133% | 100% | 169% |

Example 47

To examine the effect of one of the mutations during expression of other GLP-1 peptides, we constructed plasmids, that contained the TDH3 promoter, the gene encoding the MFalpha pre-pro-peptide in the form of either the wildtype (40G) or a 40R mutation, the gene encoding N-terminal extended GLP-1 (DVKPGQPMYDDDDK-GLP-1(9-37)[K34R] (SEQ ID NO:7) or DVKPGQP-MYDDDDK-GLP-1(9-37)[K34R,G37K]) (SEQ ID NO:43), a minimal 2 micron region for maintenance in yeast, and a selectable marker, namely the TPI gene from *S. pombe* (see FIG. 1).

These plasmids were introduced into a *Saccharomyces cerevisiae* strain lacking the TPI1 gene, allowing for selection of transformants harbouring the plasmid on media containing glucose as sole carbon source. Transformants were thereafter cultivated for 3 days in shake flasks in 5 ml relevant media and the cultivation supernatants were analyzed by LCMS for concentration of secreted GLP-1 peptide, and degree of O-glycosylation of the peptide. Table 7 shows the results including the yield of GLP-1 peptide and O-glycosylation degree of GLP-1 peptide when expressed of the wild type (wt) and of the 40R mutation.

TABLE 7

Data from expression of specific N-terminal extended GLP-1 peptide under control of Mating Factor α propeptide mutants with or without a single amino acid substitution to Arg in position 40 ($X_{40}$).

| GLP-1 peptide | $X_{40}$ of MFalpha pre-pro-peptide | Yield (% relative to wt) | O-glycosylation (% relative to wt) |
|---|---|---|---|
| GLP-1(9-37)[K34R] | Gly (wt) | 100 | 100 |
| GLP-1(9-37)[K34R] | Arg | 127 | <1 (BDL) |
| GLP-1(9-37)[K34R, G37K] | Gly (wt) | 100 | BDL |
| GLP-1(9-37)[K34R, G37K] | Arg | 143 | BDL |

Concentrations of N-terminal extended GLP-1 peptide (yield) and O-glycosylated impurity are normalised against the data from expression of the same GLP-1 peptide but under control of the Mating Factor α propeptide having the wildtype Gly as X40.
BDL: below detection limit While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method for recombinant expression in yeast of a polypeptide comprising a GLP-1 peptide, the method comprising:
culturing a yeast strain comprising a DNA sequence encoding a processing and secretion signal upstream of the sequence encoding the GLP-1 peptide,
wherein said processing and secretion signal comprises a Mating Factor α pro-peptide variant having at least one substitution in the VIGYL (SEQ ID NO: 3) sequence at positions 38-42 of formula (I):

$$X_{38}\text{-}X_{39}\text{-}X_{40}\text{-}X_{41}\text{-}X_{42} \quad (\text{SEQ ID NO: 1})$$
(I)

wherein
$X_{38}$ is V,
$X_{39}$ is selected from L, I, V or M,
$X_{40}$ is selected from G, R or K,
$X_{41}$ is selected from Y or W, and
$X_{42}$ is selected from L or I;
and wherein said Mating Factor α pro-peptide variant has less than 5 amino acid changes outside the $X_{38}\text{-}X_{42}$ sequence as compared to positions 20-85 of SEQ ID NO:2.

2. The method according to claim 1, wherein three of the amino acid residues in $X_{38}\text{-}X_{39}\text{-}X_{40}\text{-}X_{41}\text{-}X_{42}$ are identical to the corresponding amino acid residue in VIGYL (SEQ ID NO: 3).

3. The method according to claim 1, wherein $X_{40}$ is R.

4. The method according to claim 1, wherein $X_{38}$ is V, $X_{39}$ is I, $X_{40}$ is R, $X_{41}$ is Y, and $X_{42}$ is L.

5. The method according to claim 1, wherein said yeast carries at least one genetic modification reducing its capacity for O-glycosylation.

6. The method according to claim 5, wherein the PMT1 gene in said yeast is deleted.

7. The method according to claim 1, wherein said GLP-1 peptide comprises GLP-1(9-37)[K34R] or GLP-1(9-37)[K34R,G37K].

8. The method according to claim 7, wherein said GLP-1 peptide comprises an N-terminal extension.

9. A Mating Factor α pro-peptide variant having at least one substitution in the VIGYL (SEQ ID NO: 3) sequence at positions 38-42 to comprise the amino acid sequence of the general formula (I) according to claim 1,
wherein $X_{38}$ is V; $X_{39}$ is L, I, V, or M; $X_{40}$ is G, R, or K; $X_{41}$ is Y or W; and $X_{42}$ is L or I;
wherein said Mating Factor α pro-peptide variant has less than 5 amino acid residue changes outside of the $X_{38}\text{-}X_{42}$ sequence as compared to positions 20-85 of SEQ ID NO:2.

10. A GLP-1 precursor which is a fusion polypeptide comprising:
a) a pre-peptide,
b) a Mating Factor α pro-peptide variant according to claim 9;
c) optionally an extension peptide, and
d) a GLP-1 peptide.

11. An expression vector comprising a DNA sequence encoding the polypeptide according to claim 9.

12. An expression vector comprising a DNA sequence encoding the polypeptide according to claim 10.

13. A host cell comprising the expression vector according to claim 11.

14. A host cell comprising the expression vector according to claim 12.

15. The method according to claim 1, wherein said GLP-1 peptide consists of GLP-1(9-37)[K34R] or GLP-1(9-37)[K34R,G37K].

16. A GLP-1 precursor which is a fusion polypeptide according to claim 10 wherein the extension peptide is selected from the group consisting of EEK, EEAEK (SEQ ID NO:9), HK, EEAHK (SEQ ID NO:10), EEAEAHK (SEQ ID NO:11), EEAEAEAHK (SEQ ID NO:12), EEGHK (SEQ ID NO:13), EHPK, EEGEPK (SEQ ID NO:14), EEAHELK (SEQ ID NO:15), EEAHEVK (SEQ ID NO:16), EEAHEMK (SEQ ID NO:17), EEAHEFK (SEQ ID NO:18), EEAHEYK (SEQ ID NO:19), EEAHEWKEEGNTTPK (SEQ ID NO:20), EELDARLEALK (SEQ ID NO:21), QPMYKR (SEQ ID NO:22), GQPMYK (SEQ ID NO:23), PGQPMY (SEQ ID NO:24), KPGQPM (SEQ ID NO:25), LKPGQP (SEQ ID NO:26), QLKPGQ (SEQ ID NO:27), LQLKPG (SEQ ID NO:28), WLQLKP (SEQ ID NO:29), HWLQLK (SEQ ID NO:30), WHWLQL (SEQ ID NO:31), AWHWLQ (SEQ ID NO:32), EAWHWL (SEQ ID NO:33), AEAWHW (SEQ ID NO:34), EAEAWH (SEQ ID NO:35), DV, DVKPGQPLA (SEQ ID NO:36), DVKPGQPEY (SEQ ID NO:37), DVKPGEPLY (SEQ ID NO:38), DVKPGQPLY (SEQ ID NO:39), DVKPGQPLE (SEQ ID NO:40), DVKPGQPMY (SEQ ID NO:41) and DVKPGQPMYDD-DDK (SEQ ID NO:42).

* * * * *

UNITED STATES PATENT AND TRADEMARK OFFICE
CERTIFICATE OF CORRECTION

| | |
|---|---|
| PATENT NO. | : 12,024,542 B2 |
| APPLICATION NO. | : 17/687755 |
| DATED | : July 2, 2024 |
| INVENTOR(S) | : Noergaard |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 132 days.

Signed and Sealed this
Third Day of December, 2024

Katherine Kelly Vidal
*Director of the United States Patent and Trademark Office*